United States Patent
Dufour et al.

(10) Patent No.: US 11,903,770 B2
(45) Date of Patent: *Feb. 20, 2024

(54) MEDICAL IMAGING APPARATUS

(71) Applicant: KONINKLIJKE PHILIPS N.V., Eindhoven (NL)

(72) Inventors: Cecile Dufour, Paris (FR); Benoit Jean-Dominique Bertrand Maurice Mory, Medford, MA (US); Thomas Shu Yin Tang, Ontario (CA)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 377 days.

This patent is subject to a terminal disclaimer.

(21) Appl. No.: 17/062,443

(22) Filed: Oct. 2, 2020

(65) Prior Publication Data

US 2021/0015465 A1 Jan. 21, 2021

Related U.S. Application Data

(63) Continuation of application No. 15/559,460, filed as application No. PCT/EP2016/057393 on Apr. 5, 2016, now Pat. No. 10,828,014.

(51) Int. Cl.
*A61B 8/08* (2006.01)
*A61B 8/00* (2006.01)
*A61B 6/00* (2006.01)

(52) U.S. Cl.
CPC .......... *A61B 8/5261* (2013.01); *A61B 8/4245* (2013.01); *A61B 8/463* (2013.01);
(Continued)

(58) Field of Classification Search
CPC ..... A61B 8/5261; A61B 8/4245; A61B 8/463; A61B 8/483; A61B 8/5246; A61B 8/58; A61B 6/5247
See application file for complete search history.

(56) References Cited

U.S. PATENT DOCUMENTS

| | | |
|---|---|---|
| 2003/0013951 A1 | 1/2003 | Stefanescu et al. |
| 2005/0182319 A1 | 8/2005 | Glossop |

(Continued)

OTHER PUBLICATIONS

Wein et al "Integrating Diagnostic B-Mode Ultrasonography Into CT-Based Radiation Treatment Planning" IEEE Transactions on Medical Imaging vol. 26, No. 6, Jun. 2, 2007 p. 866-879.

*Primary Examiner* — Bo Joseph Peng

(57) ABSTRACT

The present invention relates to a medical imaging apparatus. The apparatus comprises an ultrasound acquisition unit including an ultrasound probe for acquiring ultrasound image data of a patient. An image data interface is provided for receiving 3D medical image data of the patient and a position determining unit for determining a position of the ultrasound probe. A calibration unit determines a transfer function between the ultrasound image data and the 3D medical image data at a plurality of positions (C) of the ultrasound probe and provides a corresponding plurality of calibrated transfer functions and calibration positions. A computation unit synchronizes the ultrasound image data and the 3D medical image data on the basis of a position of the ultrasound probe and the plurality of calibrated transfer functions, said computation unit is further adapted to weight the calibrated transfer functions on the basis of a position of the ultrasound probe.

6 Claims, 2 Drawing Sheets

(52) U.S. Cl.
CPC ............ *A61B 8/483* (2013.01); *A61B 8/5246* (2013.01); *A61B 8/58* (2013.01); *A61B 6/5247* (2013.01)

(56) References Cited

U.S. PATENT DOCUMENTS

| | | | |
|---|---|---|---|
| 2008/0009724 A1* | 1/2008 | Lee | G01S 7/52084 600/443 |
| 2010/0268085 A1* | 10/2010 | Kruecker | A61B 8/4263 600/443 |
| 2010/0286517 A1 | 11/2010 | Kamen et al. | |
| 2011/0026796 A1 | 2/2011 | Hyun et al. | |
| 2012/0215093 A1 | 8/2012 | Ji et al. | |
| 2013/0131510 A1 | 5/2013 | Toma et al. | |
| 2014/0037168 A1* | 2/2014 | Ishikawa | A61B 8/486 382/130 |
| 2014/0193053 A1 | 7/2014 | Kadoury et al. | |

* cited by examiner

MEDICAL IMAGING APPARATUS

RELATED APPLICATIONS

This application is a continuation of U.S. application Ser. No. 15/559,460, filed on Sep. 19, 2017, issued as U.S. Pat. No. 10,828,014 on Nov. 10, 2020, which is the U.S. National Phase application under 35 U.S.C. § 371 of International Application No. PCT/EP2016/057393, filed on Apr. 5, 2016. These applications and patent are hereby incorporated by reference herein.

FIELD OF THE INVENTION

The present invention relates to a medical imaging apparatus for evaluating medical image data. The present invention further relates to a medical imaging method.

BACKGROUND OF THE INVENTION

In the field of medical imaging systems, it is generally known to combine different images of a patient acquired by different medical analysis systems in order to improve the diagnostic possibilities. In particular, ultrasound systems are known which combine ultrasound images and preoperative image data of a patient derived from different analytic systems like MRT or CT. To enable a fusion of live ultrasound images of a patient with the preoperative volume data of the same patient, a position tracking system is usually utilized to spatially align the different image data.

The position tracking systems usually rely on a position calibration, e.g. based on artificial markers or feature alignment of anatomical features which can be identified in the preoperative and in the ultrasound data and which can be correlated to each other so that the alignment of the data can be determined.

The alignment of the ultrasound image data and the medical image data can be based on ultrasound probe calibration information to provide a spatial alignment of the image data as e.g. known from US 2010/0286517 A1.

The accuracy of the spatial synchronization of the ultrasound data and the medical image data is dependent on the distance of the ultrasound probe and the calibration position so that a misalignment of the synchronization increases with a distance from the calibration position. Usually if a misalignment occurs, a recalibration of the image data and the tracking system is performed, however, a misalignment at the previously calibrated position will occur again.

SUMMARY OF THE INVENTION

It is therefore an object of the invention to provide an improved medical imaging apparatus and a corresponding improved medical imaging method for synchronizing different medical image data with an improved accuracy.

According to one aspect of the present invention, a medical imaging apparatus is provided, comprising:
 an ultrasound acquisition unit including an ultrasound probe for acquiring ultrasound image data of a patient,
 an image data interface for receiving 3D medical image data of the patient,
 a position determining unit for determining a position of the ultrasound probe,
 a calibration unit adapted to determine a transfer function between the ultrasound image data and the 3D medical image data at a plurality of positions of the ultrasound probe and adapted to provide a corresponding plurality of calibrated transfer functions and calibration positions, and
 a computation unit adapted to synchronize the ultrasound image data and the 3D medical image data on the basis of a position of the ultrasound probe and the plurality of calibrated transfer functions.

According to another aspect of the present invention, a medical imaging method for combining different medical image data is provided comprising the steps of:
 acquiring ultrasound data of a patient by means of an ultrasound probe,
 receiving 3D medical image data of the patient,
 determining a position of the ultrasound probe by means of a position determining unit,
 determining a transfer function between the ultrasound image data and the medical image data at a plurality of positions of the ultrasound probe and providing a corresponding plurality of calibrated transfer functions and calibration positions, and
 synchronizing the ultrasound image data and the 3D medical image data on the basis of a position of the ultrasound probe and the plurality of transfer functions.

Preferred embodiments of the invention are defined in the dependent claims. It shall be understood that the claimed method has similar and/or identical preferred embodiments as the claimed device and as defined in the dependent claims.

The present invention is based on the idea to determine a plurality of transfer functions linking the ultrasound image data and the 3D medical image data with each other for a plurality of positions of the ultrasound probe in order to provide corresponding calibration positions of the ultrasound probe on the basis of which the ultrasound image data and the 3D medical image data is synchronized. Since different calibration positions are determined by means of the calibration unit, the distance of the ultrasound probe to one of the calibration positions can be considered so that the accuracy of the spatial synchronization of the ultrasound image data and the 3D medical image data can be improved. Since the different calibration positions and the determined plurality of calibrated transfer functions are simultaneously or at the same time utilized for the synchronization of the image data, the spatial alignment of the different image data can be improved for a large area of the patient's body.

Consequently, the accuracy of the spatial synchronization of the ultrasound image data and the 3D medical image data can be improved.

In accordance to the present invention, the computation unit is adapted to weight the calibrated transfer functions on the basis of a position of the ultrasound probe. This is a possibility to utilize the different calibrated transfer functions depending on the position of the ultrasound probe, so that the optimal calibrated transfer function can be considered for synchronizing the image data.

In a preferred embodiment, the computation unit is adapted to weight the calibrated transfer functions on the basis of a distance between the ultrasound probe and a plurality of the calibration positions. This is a possibility to improve the synchronization, since the accuracy of the synchronization depends on the distance to the calibration positions.

In a preferred embodiment, the computation unit is adapted to weight the calibrated transfer functions on the basis of a distance between a predefined position at a tip of the ultrasound probe and a plurality of the calibration positions. This is a possibility to determine the calibrated transfer functions on the basis of a defined reference position at the ultrasound probe, so that a precise definition of the transfer function can be achieved with low technical effort.

In a further preferred embodiment, the computation unit is adapted to weight the calibrated transfer functions on the basis of a distance between a predefined position within the ultrasound image data and a plurality of the calibration positions. This is a possibility to determine the calibrated transfer functions on the basis of a defined reference position within the ultrasound image data, so that a precise definition of the transfer function can be achieved with low technical effort.

In a further preferred embodiment, the predefined position within the ultrasound image data to a plurality of the calibration positions is a center of the ultrasound image data. The center of the ultrasound image data corresponds to a center of the field of view of the ultrasound probe or an axis of symmetry of the ultrasound cone. This is a possibility to define a reference point of the ultrasound image data so that the calibrated transfer functions can be determined precisely with low technical effort.

In a preferred embodiment, the computation unit is adapted to weight the calibrated transfer functions by means of relative weight factors. The relative weight factors have preferably a value between 1 and 0. In other words, the relative weight factors are normalized. This is a possibility to achieve a weighting of the calibrated transfer functions, wherein each transfer function can be considered on the basis of the respective relevance.

In a preferred embodiment, the computation unit is adapted to weight the calibrated transfer functions on the basis of absolute weight factors. The absolute weight factors have the value of either 1 or 0. This is a possibility to further reduce the computation effort of the synchronization of the image data, since only those calibration transfer functions having the highest relevance are considered. In particular, the transfer function having the closest calibration position to the current position is considered as the only calibrated transfer function and the other calibrated transfer functions are not considered.

In a preferred embodiment, the calibration unit is adapted to determine a 3D rigid transformation for each calibration position. The transfer function is determined on the basis of the rigid transformation or a 3D fixed transformation between the different image data for each calibration position. This is a possibility to determine the spatial synchronization precisely with low technical effort, since a fixed transformation is provided for each calibration position.

In a preferred embodiment, the computation unit is adapted to determine a general transfer function for a current position of the ultrasound probe on the basis of the calibrated transfer functions weighted by means of weight factors. This is a possibility to precisely determine the synchronization of the ultrasound image data and the medical image data, since a single general transfer function is determined on the basis of different calibration information.

In a preferred embodiment, the medical imaging apparatus further comprises an image interface for providing fused image data on the basis of the synchronized ultrasound image data and the 3D medical image data to a display unit. This is a possibility to display the combined image data.

As mentioned above, the medical imaging apparatus for combining different medical image data and the corresponding method can improve the accuracy of the spatial synchronization of the ultrasound and medical image data since the synchronization is based upon a plurality of calibrated transfer functions, which correspond to the calibration at different positions of the ultrasound probe. This is a possibility to utilize at least one transfer function which provides the best calibration and synchronization so that the spatial alignment of the image data can be improved. The definition of the different calibrated transfer functions corresponding to different calibration positions can further be utilized for a weighting based on the position of the ultrasound probe and/or a distance to the calibration positions so that a resulting overall or general transfer function can be determined on the basis of different calibration positions and the respective position of the ultrasound probe. Hence, the accuracy and the technical effort for fusing the ultrasound and medical image data can be improved.

BRIEF DESCRIPTION OF THE DRAWINGS

These and other aspects of the invention will be apparent from and elucidated with reference to the embodiments described hereinafter. In the following drawings

DETAILED DESCRIPTION OF THE INVENTION

Figure 1:
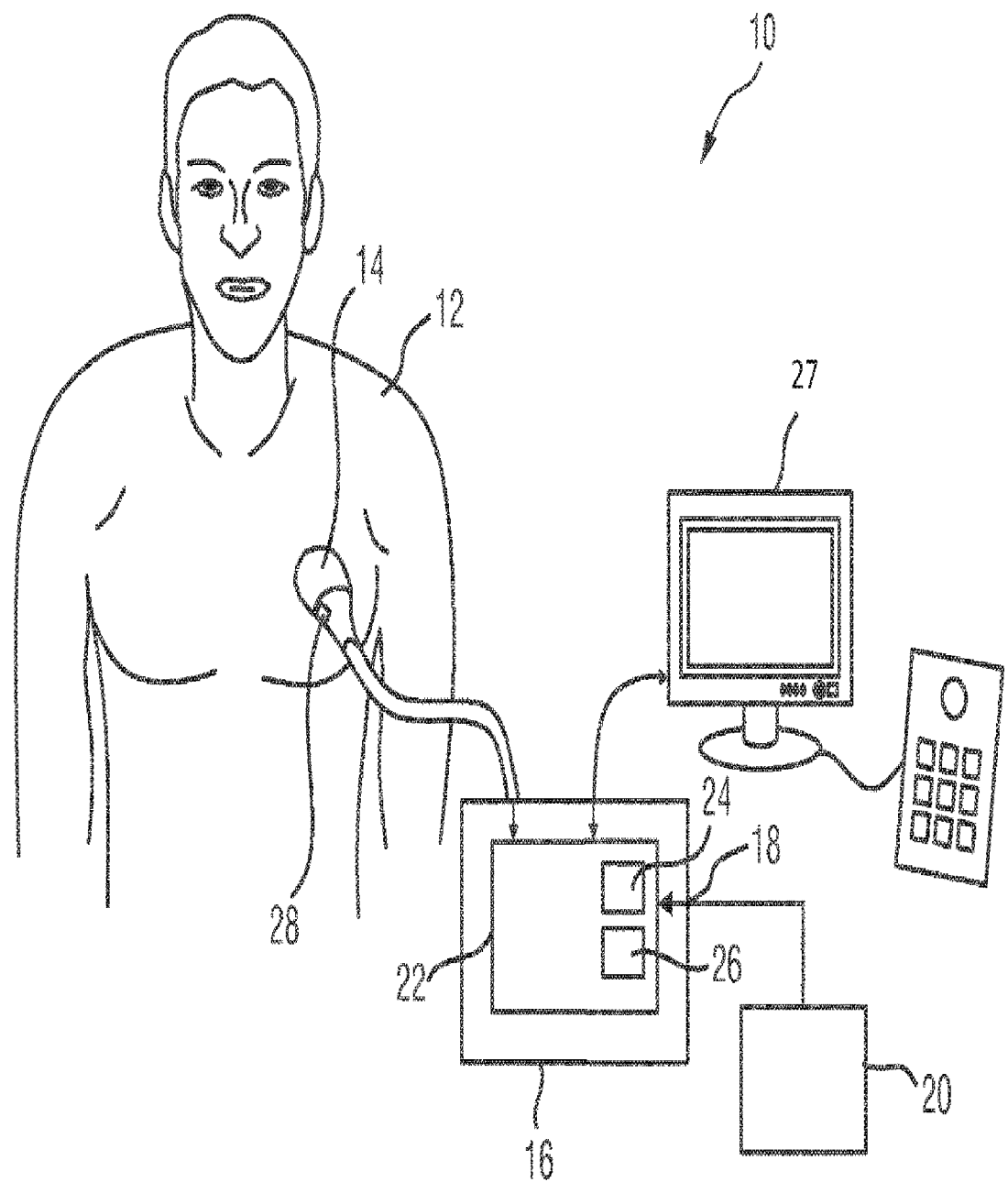
FIG. 1 shows a schematic representation of a medical imaging apparatus in use to scan a volume of a patient's body.

FIG. 1 shows a schematic illustration of a medical imaging apparatus generally denoted by 10. The medical imaging apparatus 10 is applied to inspect a volume of an anatomical site, in particular an anatomical site of a patient 12. The medical imaging apparatus 10 comprises an ultrasound probe 14 having at least one transducer array including a multitude of transducer elements for transmitting and receiving ultrasound waves. The transducer elements are preferably arranged in a 2D array, in particular for providing multidimensional image data.

The medical imaging apparatus 10 comprises in general an image processing apparatus 16 connected to the ultrasound probe 14 for evaluating the ultrasound data received from the ultrasound probe and for combining or correlating the ultrasound images with preoperative images of the patient 12. The image processing apparatus 16 comprises an image interface 18 for receiving the preoperative 3D medical image data from a data base 20 or an external analysis and imaging apparatus 20. The preoperative image data is preferably computer tomography image data (CT), magnetic resonance tomography image data (MRT), X-ray image data or preoperative 3D ultrasound image data. The image processing apparatus 16 comprises an image processing unit 22 connected to the ultrasound probe 14 and to the image interface 18 for evaluating the ultrasound data and for providing ultrasound image data from the volume or object of the patient which is analyzed by the ultrasound probe 14 and for combining the preoperative 3D medical image data received from the image interface 18 with the ultrasound data received from the ultrasound probe 14.

The medical imaging apparatus 10 further comprises a position determining unit 28 attached to the ultrasound probe 14 for determining a position of the ultrasound probe 14. The position determining unit determines the absolute position of the ultrasound probe, e.g. by means of electromagnetic tracking in order to determine a position and/or a movement of the ultrasound probe 14.

An image processing unit 22 comprises a calibration unit 24 for calibrating different positions of the ultrasound probe with respect to the 3D medical image data and to provide corresponding calibration positions of the ultrasound probe 14. The calibration unit 24 determines at the different calibration positions transfer functions between the ultrasound image data determined by the ultrasound probe 14 at the calibration position and the corresponding 3D medical image data. The transfer function between the ultrasound image data and the 3D medical image data is a mathematic transformation between corresponding spatial positions in the ultrasound image data and the 3D medical image data such as voxels so that each spatial or three-dimensional position in the ultrasound image data and the 3D medical image data can be correlated with each other.

The calibration unit determines a transfer function at each different calibration position so that the calibration unit 22 provides a plurality of transfer functions for calibrating the medical imaging apparatus 10. The calibration may be based on artificial markers, which are disposed at the patient's body and which can be identified in the ultrasound image data and the 3D medical image data so that a pairing of the markers and corresponding three-dimensional or spatial positions of the markers in the different image data allow to determine a transfer function as a three-dimensional transformation in order to calibrate the position and the image data with each other. Another possibility to calibrate the medical imaging apparatus 10 is to identify anatomical features within the patient's body which are detectable in the ultrasound image data and the 3D medical image data such as vessel bifurcations so that the spatial or three-dimensional position of these identified anatomical features can be used to determine a three dimensional transformation between the different image data in order to determine the respective transfer function. The so determined transfer functions can be stored for the different calibration positions and can be utilized for a synchronization of the ultrasound image data and the three-dimensional medical image data.

The image processing unit 22 further comprises a computation unit 26 for synchronizing (real time registration) the ultrasound image data and the 3D medical image data on the basis of a position of the ultrasound probe and the plurality of calibrated transfer functions. The computation unit 26 receives the current position of the ultrasound probe 14 from the position determining unit 28 and calculates a general transfer function or a general three-dimensional transformation between the ultrasound image data at the current position and the corresponding three-dimensional medical image data in order to synchronize the ultrasound image data determined at the current position with the corresponding 3D medical image data received from the data base 20 or the imaging apparatus 10.

The image processing unit 22 determines fused image data as correlated or superimposed ultrasound image data and 3D medical image data on the basis of the synchronization received from the computation unit 26 at the current position of the ultrasound probe 14. The image processing unit 22 is connected to a display unit 27 and provides the fused image data to the display unit 27 for displaying the respectively fused image data.

Since the synchronization of the ultrasound image data and the 3D medical image data for the current position of the ultrasound probe 14 is based on the plurality of transfer functions determined at the different calibration positions of the ultrasound probe 14, the synchronization and the calibration in general can be improved so that the alignment and the synchronization of the different image data can be provided with an improved precision.

The calibration unit 24 determines at the different calibration positions a fixed or rigid three-dimensional transformation, wherein the computation unit 26 determines a general transfer function for the current position of the ultrasound probe 14 with respect to each calibration position so that the synchronization is based on the plurality of calibration transfer functions. The calibration transfer functions are weighted by means of weight factors corresponding to the respective distance of the current position of the ultrasound probe to the respective calibration positions to the general transfer function.

The different weight factors are preferably relative weight factors and have a value between 1 and 0, wherein the sum of the relative weight factors is 1. Alternatively, the weight factors are absolute weight factors having a value of 1 or 0, wherein merely one of the weight factors is 1 and the others are 0 so that merely the transfer function of the closest calibration position is utilized.

Figure 2:
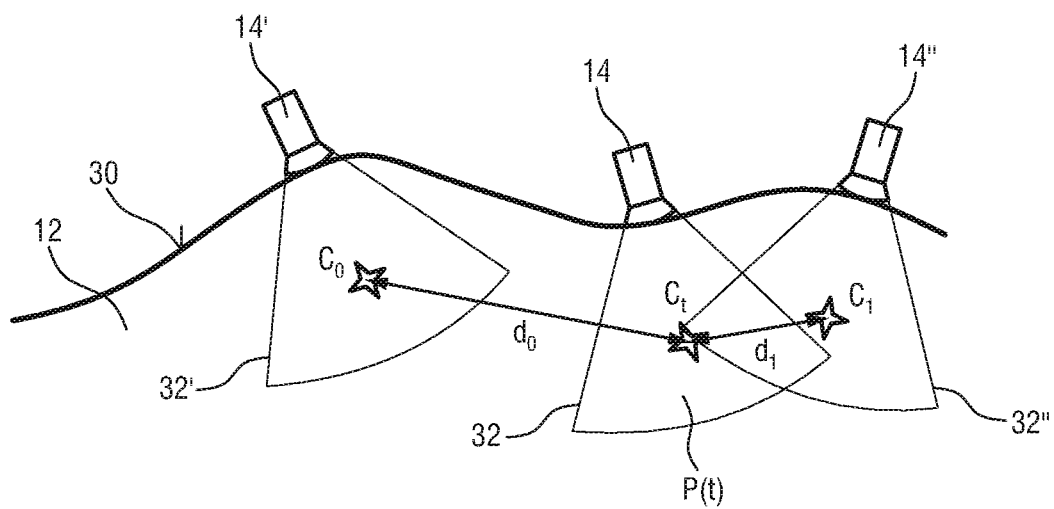
FIG. 2 shows a schematic diagram illustrating the calibration at different positions of the ultrasound probe and a current position of the ultrasound probe.

FIG. 2 shows a schematic sectional diagram illustrating the calibration at different positions of the ultrasound probe 14 and a current position of the ultrasound probe 14.

In FIG. 2, the ultrasound probe 14 is shown together with a field of view 32 within the patient's body 12 from which the ultrasound image data is acquired as three-dimensional ultrasound data.

The different calibration positions of the ultrasound probe 14', 14" are determined with respect to a center position $C_0$, $C_1$ of the ultrasound data cone or in the center of the field of view 32', 32". Alternatively, any predefined positions within the ultrasound data cone can be defined as reference position or any position at a tip of the ultrasound probe 14 preferably a center position at the tip can be defined as reference position.

In a first step, a transfer function $T(t_0)$ linking the ultrasound image data and the 3D medical image data to each other are determined, corresponding to a spatial synchronization between the ultrasound image data and the 3D medical image data. Further, a rigid 3D transformation or a fixed 3D transformation $Q_0$ is determined as $Q_0 = T(t_0)/P(t_0)$, wherein $P(t_0)$ is the position of the ultrasound probe 14' at the position $C_0$. Corresponding to each calibration position of the ultrasound probe 14, the relationship, i.e. the transfer function between the ultrasound data and the 3D medical image data or the spatial transformation of the different image data can be written as $$T(t) = Q_i * P(t) \tag{1}$$

wherein $T(t)$ is the transfer function, $Q_i$ is the rigid or fixed transformation for the respective calibration position and $P(t)$ is the current position of the ultrasound probe 14. After the calibration at the first calibration position $C_0$ is performed, additional calibration steps at further positions $C_1$ are performed in order to achieve different calibration positions and different transfer functions $T(t_i)$.

In view of FIG. 2, two calibration transfer functions with respect to two calibration positions $C_0$, $C_1$ can be calculated linking or connecting the ultrasound data and the 3D medical image data:

$$T_{cal0}(t) = Q_0 * P(t) \tag{2}$$

$$T_{cal1}(t) = Q_1 * P(t) \tag{3}$$

wherein each of these calibration transfer functions correspond to a transfer function with respect to the respective calibration position. On the basis of these calibration transfer functions, a general transformation or a general transfer function T(t) can be calculated as a convex combination of both calibration transfer functions:

$$T(t)=(1-a)T_{cal0}(t)+a\ T_{cal1}(t)\ 0\le a\le 1 \quad (4)$$

wherein a is a weight factor considering the distance of the current position $C_t$ of the probe 14 with respect to the two calibration positions $C_o$, $C_1$. In a generalized form, the general transformation T(t) for n calibration steps and calibration positions can be expressed as:

$$T(t)=a_0*T_{cal0}(t)+\ldots+a_iT_{cali}(t)+\ldots+a_nT_{caln}(t) \quad (5)$$

with $a_0+\ldots+a_i+\ldots+a_n=1$ and $a_i\ge 0$.

The general transfer functions including the weight factors a and the weighted or fixed transformation $Q_n$ in the form of formula 1 can be expressed as:

$$T(t)=(a_0Q_0+\ldots+a_iQ_i+\ldots+a_nQ_n)P(t) \quad (6)$$

The weight factors a can be computed based on a distance from the center positions $C_0$, $C_1$ in the field of view 32', 32" from the current position $C_t$ of the field of view 32. On the basis of the distance, the calibration transfer function of a calibration position which is closer to the current position used is considered more and has as a large weight in the general transformation function T(t). Since the position determining unit 28 of the ultrasound probe 14 determines the position at the calibration positions $C_0$, $C_1$ and the current position, a respective distance is at any time available and the respective distance to each of the calibration positions can be computed as: $d(C_i)=d(C_i, C(t))$.

For the case that an absolute weighting of the transfer functions is utilized, the calibration positions having the smallest distance $d(C_n)$ are set to $a_n=1$ and $a_n=0$ otherwise. A such absolute weighting would merely consider the calibration which has the smallest distance to the current position and would not consider all other calibration positions.

Alternatively, a relative weighting can be utilized, whereas the transfer function of the closer calibration position is considered more with a higher weight factor a and the calibration transfer function of a calibration position with a higher distance is less considered with a lower weight factor a. For the particular case of n=2, the weights of the weight factors a are set as follows:

$$a_i=d(Cal_j)/(d(Cal_i)+d(Cal_j)) \quad (7)$$

wherein the sum of the weight factors a, is always set to 1.

Figure 3:
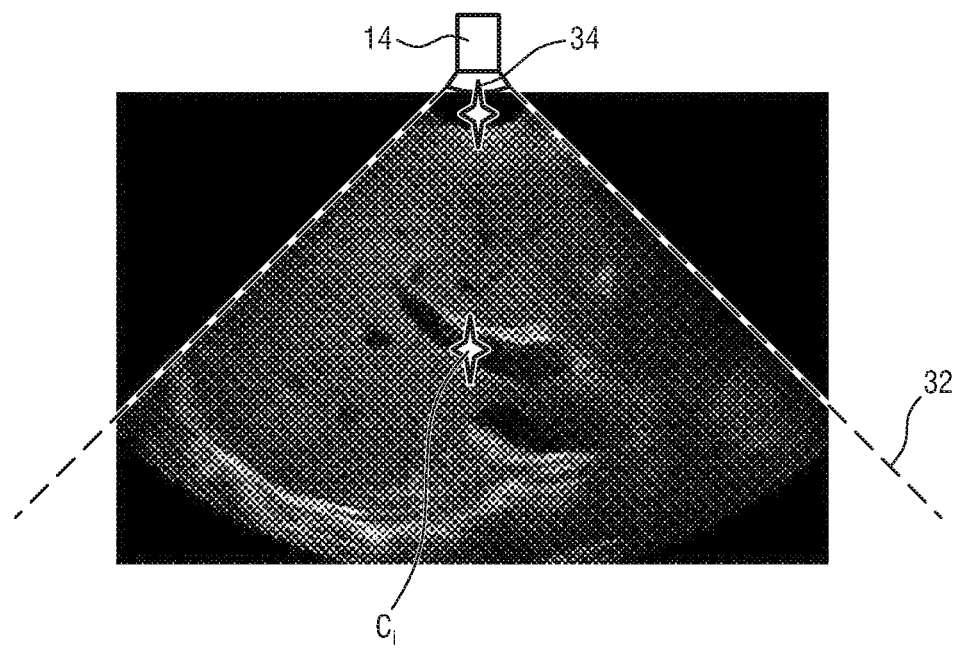
FIG. 3 shows an ultrasound image including a central reference positions for determining the calibration position.

In FIG. 3, an ultrasound image corresponding to the ultrasound image data is schematically shown in a field of view 32 of the ultrasound probe 14. The ultrasound probe 14 determines the ultrasound image data in the field of view 32, wherein in the center of the field of view 32 or the ultrasound data cone, the central position $C_i$ is defined as a reference position of the ultrasound image data. By means of these definitions, the transfer functions and the respective synchronization of the ultrasound image data and the three-dimensional medical image data can be achieved with high precision.

Alternatively, a center position 34 at the tip of the ultrasound probe 14 can be used as a reference position for the calibration and the synchronization.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. A method for combining different medical image data, the method comprising:
   acquiring ultrasound data with an ultrasound probe;
   receiving three dimensional (3D) medical image data;
   determining a position of the ultrasound probe with an electromagnetic tracker;
   determining a transfer function between the ultrasound image data and the 3D medical image data at a plurality of positions (C) of the ultrasound probe and providing a corresponding plurality of calibrated transfer functions ($T_{cal0}$, $T_{cal1}$), wherein the plurality of calibrated transfer functions are weighted by relative weight factors, and wherein the relative weight factors have corresponding values between zero and one; and
   synchronizing the ultrasound image data and the 3D medical image data based, at least in part, on a position of the ultrasound probe and the plurality of calibrated transfer functions.

2. The method of claim 1, wherein the calibrated transfer functions are weighted based, at least in part, on the position of the ultrasound probe.

3. The method of claim 1, further comprising determining a plurality of calibration positions, wherein synchronizing the ultrasound image data and the 3D medical image data is further based on the plurality of calibration positions.

4. The method of claim 3, further comprising determining a 3D rigid transformation (Q) for each of the plurality of calibration positions.

5. The method of claim 1, further comprising:
   fusing the image data and the 3D medical image data based, at least in part, on synchronization of the image data and the 3D data to generate fused image data; and
   displaying the fused image data on a display.

6. A method for combining different medical image data, the method comprising:
   acquiring ultrasound data with an ultrasound probe;
   receiving three dimensional (3D) medical image data;
   determining a position of the ultrasound probe with an electromagnetic tracker;
   determining a transfer function between the ultrasound image data and the 3D medical image data at a plurality of positions (C) of the ultrasound probe and providing a corresponding plurality of calibrated transfer functions ($T_{cal0}$, $T_{cal1}$); and
   synchronizing the ultrasound image data and the 3D medical image data based, at least in part, on a position of the ultrasound probe and the plurality of calibrated transfer functions wherein the plurality of calibrated transfer functions are weighted by absolute weight factors and the absolute weight factors have corresponding values of zero or one.

* * * * *